(12) United States Patent
Tsujita et al.

(10) Patent No.: US 7,573,977 B2
(45) Date of Patent: Aug. 11, 2009

(54) MAMMOGRAPHIC APPARATUS

(75) Inventors: Kazuhiko Tsujita, Otawara (JP); Shingo Kanemitsu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 48 days.

(21) Appl. No.: 11/668,693

(22) Filed: Jan. 30, 2007

(65) Prior Publication Data
US 2007/0183566 A1 Aug. 9, 2007

(30) Foreign Application Priority Data
Jan. 31, 2006 (JP) .............................. 2006-023845

(51) Int. Cl.
*H05G 1/02* (2006.01)
(52) U.S. Cl. ........................................ 378/37; 378/197
(58) Field of Classification Search .................. 378/21, 378/24, 27, 37, 196, 197
See application file for complete search history.

(56) References Cited

U.S. PATENT DOCUMENTS

| | | | | |
|---|---|---|---|---|
| 5,018,176 A | * | 5/1991 | Romeas et al. ................ 378/37 |
| 5,872,828 A | * | 2/1999 | Niklason et al. ............... 378/23 |
| 6,375,352 B1 | * | 4/2002 | Hewes et al. ................. 378/196 |
| 6,882,700 B2 | * | 4/2005 | Wang et al. .................... 378/37 |
| 6,928,139 B2 | * | 8/2005 | Muller et al. .................. 378/37 |
| 6,999,554 B2 | * | 2/2006 | Mertelmeier ................. 378/37 |
| 2004/0109529 A1 | | 6/2004 | Eberhard et al. | |

FOREIGN PATENT DOCUMENTS

| | | |
|---|---|---|
| JP | 2003-305031 | 10/2003 |
| JP | 2004-188200 | 7/2004 |

* cited by examiner

*Primary Examiner*—Allen C. Ho
(74) *Attorney, Agent, or Firm*—Oblon, Spivak, McClelland, Maier & Neustadt, P.C.

(57) ABSTRACT

A mammographic apparatus for taking an image of a breast by detecting an X-ray radiated from an X-ray tube and transmitted a breast of a subject by means of an X-ray detector. The mammographic apparatus includes a column, a first support frame arranged, for rotation about a rotary axis, on the column and supporting the X-ray tube, a second support frame arranged, for rotation about the rotary axis, on the column and supporting the X-ray detector, and a mechanism for selectively switching over between a first mode that the second support frame is rotated by a rotation force of the first support frame and a second mode that the first support frame is rotated independently of the second support frame.

6 Claims, 8 Drawing Sheets

FIG. 10A  FIG. 10B  FIG. 10C
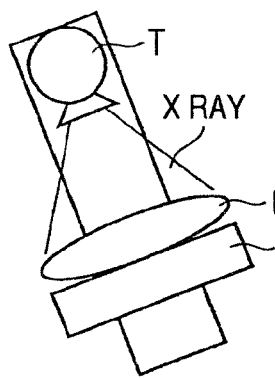
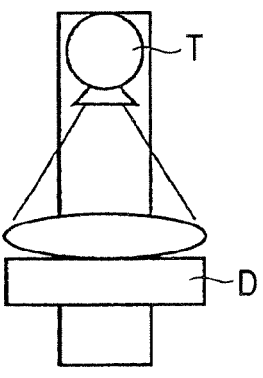
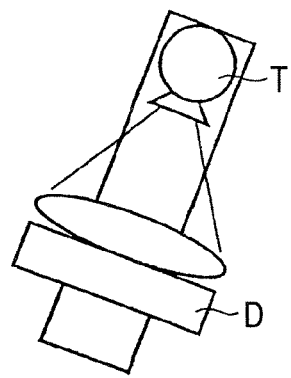
FIG. 11
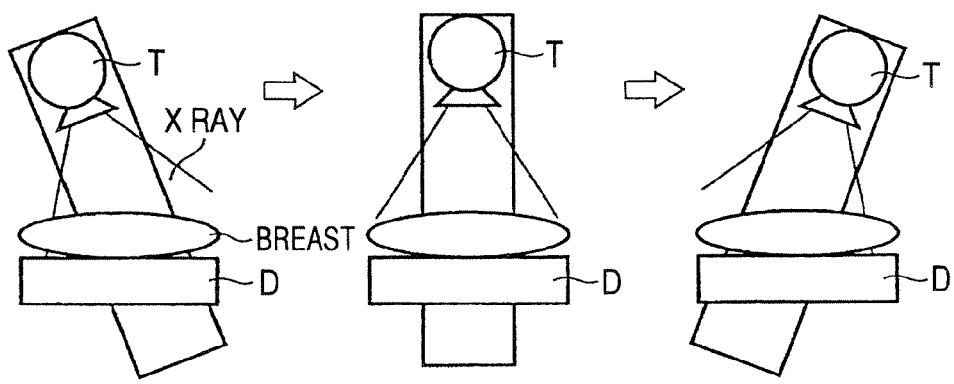

MAMMOGRAPHIC APPARATUS

CROSS-REFERENCE TO RELATED APPLICATIONS

This application is based upon and claims the benefit of priority from prior Japanese Patent Application No. 2006-023845, filed Jan. 31, 2006, the entire contents of which are incorporated herein by reference.

BACKGROUND OF THE INVENTION

1. Field of the Invention

The present invention relates to a mammographic apparatus for taking an image of a breast by detecting the X-ray radiated from an X-ray tube and transmitted through a breast of a subject by an X-ray detector.

2. Description of the Related Art

In the basic radiography with a mammographic apparatus, the X-ray tube T and the X-ray detector D are placed opposed to each other in taking an image at any angle, as shown in FIGS. 10A, 10B and 10C, for example.

Meanwhile, there is a tomosynthetic radiography (tomo-radiography) as means for obtaining a three-dimensional image by use of a mammographic apparatus.

In the tomosynthetic radiography, it is a practice to take an image while rotating the X-ray tube T relative to the breast in the state fixing the breast and the X-ray detector D, as shown in FIG. 11, as an example.

For this reason, the mammographic apparatus, capable of coping with the two radiographic schemes, is required to perform both operations of rotating the X-ray tube T and the X-ray detector D in a synchronous fashion and of rotating the X-ray tube T while placing the X-ray detector at rest.

In order to realize the operations, the X-ray tube T and the X-ray detector D are necessarily arranged on separate frames so that the frames can be rotated independently.

In this case, if desired to enhance the concentricity of rotation path between the X-ray tube T and the X-ray detector D, typically the frames are held for separate rotation about the common rotary axis. In this case, the frames are rotated by separate motors.

In such an arrangement, there is a need to synchronously control the two motors with accuracy in rotating the X-ray tube T and the X-ray detector D in a synchronous fashion. This, however, is not easy to realize.

Meanwhile, there is proposed a structure to move a frame fixed with an X-ray tube along an arcuate path (see JP-A 2003-305031, for example). However, with this structure, deterioration is encountered in the rotation-path concentricity of between the X-ray tube T and the X-ray detector D.

In this manner, there is conventionally a difficulty in implementing a synchronous rotation while enhancing the rotation-path concentricity of between the X-ray tube T and the X-ray detector D.

BRIEF SUMMARY OF THE INVENTION

In such situations, there is a desire for achieving well the concentricity and enabling a synchronous rotation with accuracy and easiness while enabling both operations of rotating the X-ray tube device and the detector unit in a synchronous fashion and of rotating the X-ray tube device with the detector unit placed at rest.

A mammographic apparatus according to a first aspect of the present invention is for taking an image of a breast by detecting an X-ray radiated from an X-ray tube and transmitted a breast of a subject by means of an X-ray detector, the mammographic apparatus comprising: a column; a first support frame arranged, for rotation about a rotary axis, on the column and supporting the X-ray tube; a second support frame arranged, for rotation about the rotary axis, on the column and supporting the X-ray detector; and a mechanism for selectively switching over between a first mode that the second support frame is rotated by a rotation force of the first support frame and a second mode that the first support frame is rotated independently of the second support frame.

Additional objects and advantages of the invention will be set forth in description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIGS. 10A, 10B and 10C are views each showing a positional relationship of between an X-ray tube and an X-ray detector, in taking an image according to the basic radiography; and FIG. 11 is a view showing a positional relationship of between the X-ray tube and the X-ray detector, in taking an image according to tomosynthetic radiography.

DETAILED DESCRIPTION OF THE INVENTION

With reference to the drawings, explanation will now be made on embodiments.

First Embodiment

Figure 1:
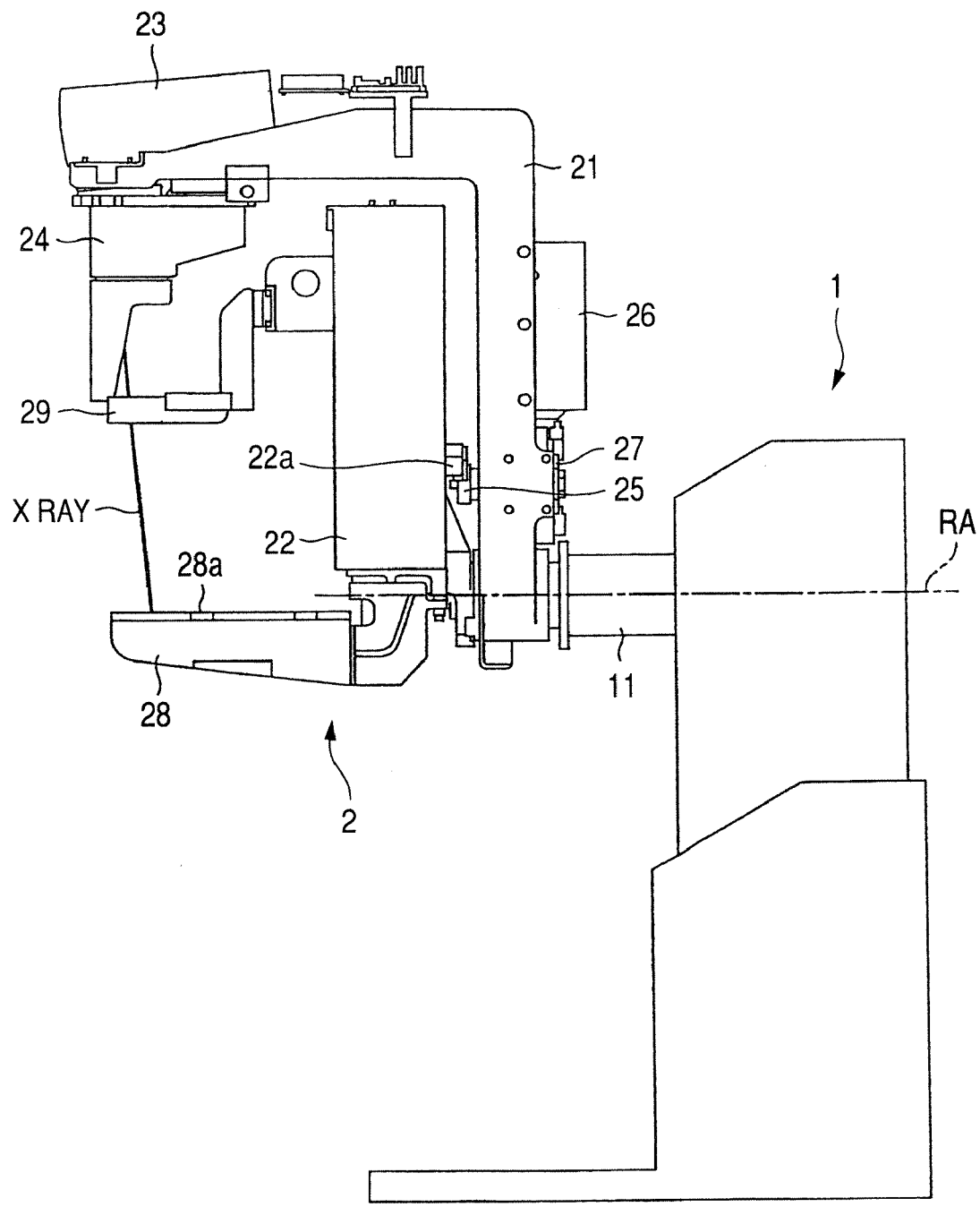
FIG. 1 is a view showing a construction of a mammographic apparatus according to a first embodiment of the present invention.

FIG. 1 is a view showing a construction of a mammographic apparatus according to a first embodiment.

The mammographic apparatus shown in FIG. 1 includes a column unit 1 and a C-arm unit 2. The C-arm unit 2 is mounted on a shaft 11 projecting from the column unit 1.

Thus, the column unit 1 supports the C-arm unit 2 rotatable about a rotary axis RA provided by the axis of the shaft 11.

The C-arm unit 2 has two frames 21, 22 that constitute an arm body. The frames 21, 22 are supported by the column unit 1 so that they can separately rotate about the rotary axis RA. The frame 21 is arranged with an X-ray tube device 23, a restriction 24, a spur gear 25, a motor 26 and a reduction gear 27, as shown in FIG. 1. The frame 22 is arranged with a detector unit 28 and a pusher plate 29, as shown in FIG. 1. Meanwhile, an arc gear 22a is provided on the frame 22.

The X-ray tube device 23 incorporates an X-ray tube so that the X-ray tube can radiate an X-ray toward the detector unit 28. The restriction 24 is to restrict the field-of-irradiation of the X-ray radiated from the X-ray tube device 23.

The detector unit 28 is made flat in its upper surface as viewed in FIG. 1, which surface provides a photographic platform 28a. The pusher plate 29 is arranged opposite to the photographic platform 28a. The pusher plate 29 is variable in the spacing to the photographic platform 28a, due to a movement mechanism built in the frame 22. This allows the pusher plate 29 to depress a breast rested upon the photographic platform 28a. The detector unit 28 incorporates an X-ray detector to detect an X-ray radiated from the X-ray tube device 23 and transmitted through the breast. The X-ray detector is to output an image signal in accordance with an X-ray image which the detected X-ray represents.

Figure 2:
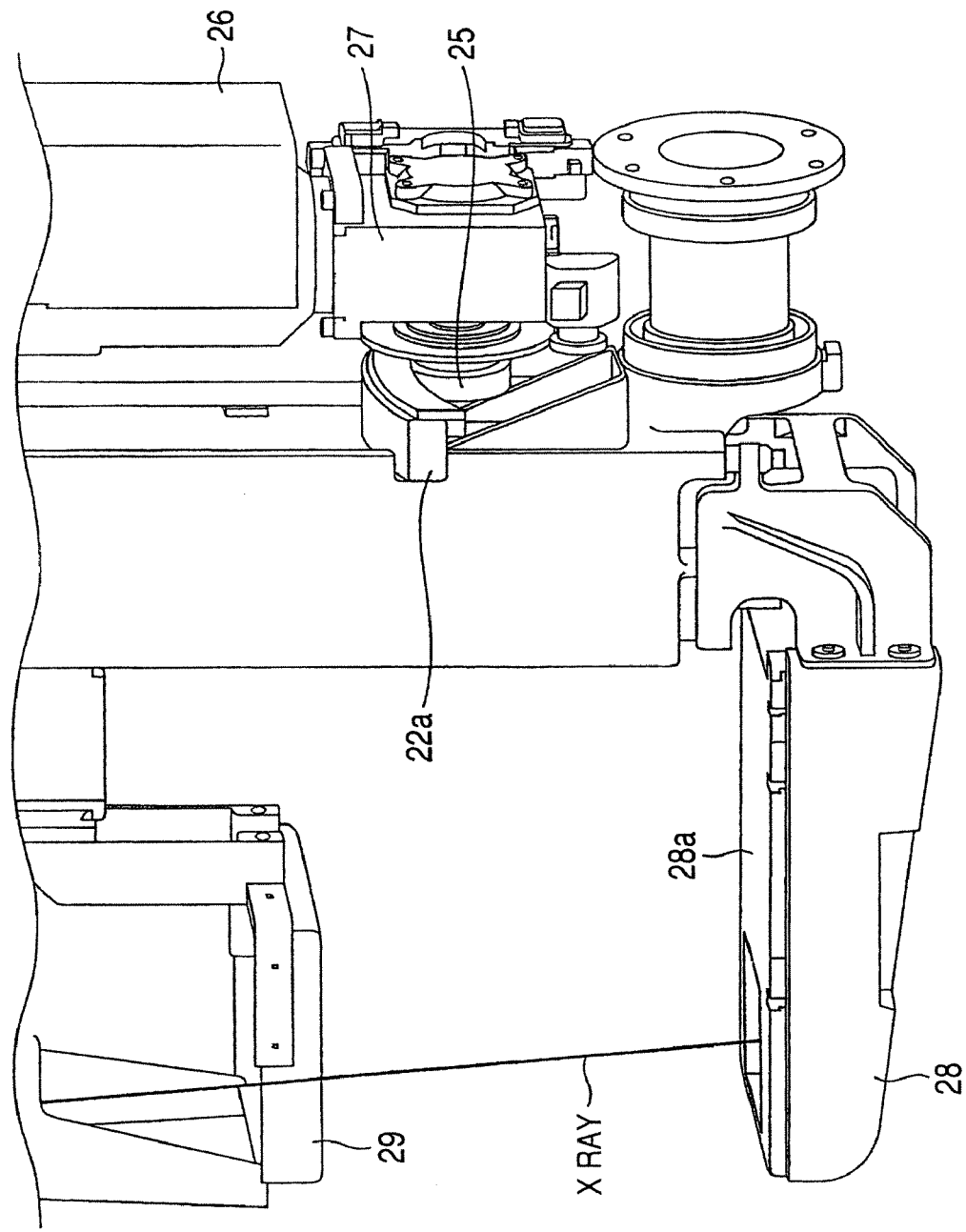
FIG. 2 is a perspective view showing a FIG. 1 spur gear and arcuate gear with magnification.

FIG. 2 is a perspective view showing a spur gear 25 and arc gear 22a with magnification.

The arc gear 22a is formed integral with the frame 22 in a state protruding from the frame 22, as shown in FIG. 2. The arc gear 22a has a curved surface on the closer side to the rotary axis RA and extending along an arc about the rotary axis RA, thus being structured by forming grooves in the curved surface. The arc gear 22a is in mesh with the spur gear 25.

The rotation force of the motor 26 is delivered to the spur gear 25 through the reduction gear 27. The reduction gear 27 is to deliver the rotation force of the motor 26 to the spur gear 25 by increasing the torque through reducing the rotation plate thereof. The reduction gear 27 has a well-known self-locking function. Namely, the reduction gear 27 suppresses the spur gear 25 from rotating when the motor 26 is shut down.

Figure 3:
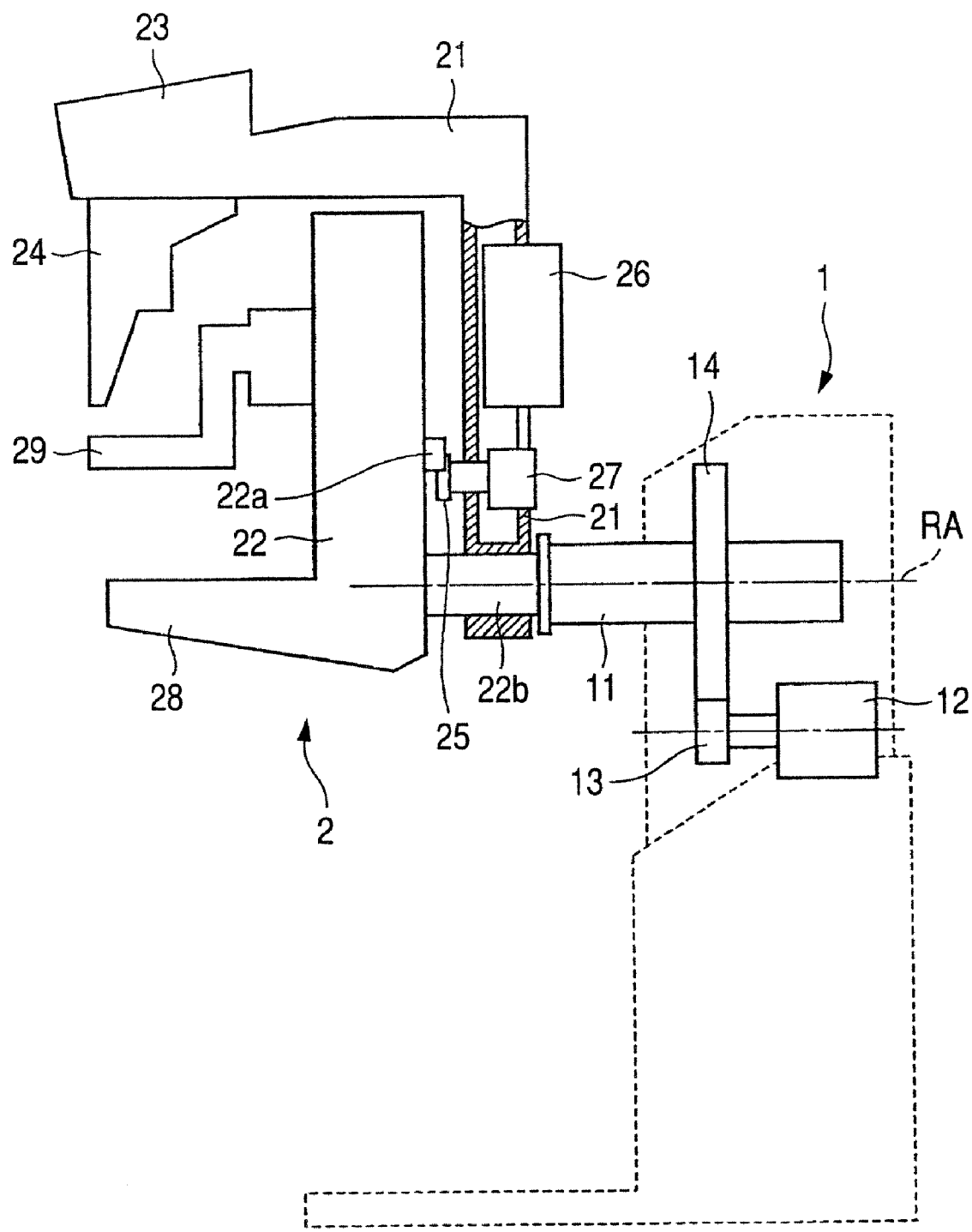
FIG. 3 is a view showing a FIG. 1 frame, by partly broken away, and an internal arrangement of a column unit.

FIG. 3 is a view showing the frame 21, by partly broken away, and the internal arrangement of the column unit 1.

The frame 21 is formed, at its end, with a through-hole in which a shaft 22b projecting from the frame 22 is inserted. The frame 21 is rotatable regardless of the shaft 22b by the well-known technique, e.g. arranging a bearing between the frame 21 and the shaft 22b.

The shaft 22b is formed integral with the frame 22 or secured to the frame 22. The shaft 22b is secured to the shaft 11 such that its axis is coincident with the rotary axis RA.

The shaft 11 is rotatably supported at the inside of the column unit 1. In the column unit 1, there are arranged a motor 12, a gear 13 and a gear 14. The gear 13 and the gear 14 are in mesh with each other. The gear 13 is attached to the motor 12. The gear 14 is fixed on the shaft 11.

In this arrangement, when the motor 12 is rotated in a state the motor 26 is shut down, the rotation force of the motor 12 is delivered through the gears 13, 14 to thereby rotate the shafts 11, 22b. As a result, the frame 22 is rotated. Due to the rotation of the frame 22, the arc gear 22a is caused to move. Because the arc gear 22a is in mesh with the spur gear 25 while the reduction gear 27 is self-locked, the moving force of the arc gear 22a is directly delivered to the reduction gear 27 through the spur gear 25. Consequently, the frame 21 is pushed by means of the reduction gear 27, thus causing the frame 21 to rotate. Namely, in this state, the frames 21, 22 rotate periodically. In this case, because both the frames 21, 22 rotate about the rotary axis RA, concentricity is achieved well. Meanwhile, because the frames 21, 22 are rotated only based on the rotation force of the motor 12, there is no need to control a plurality of motors synchronously. Accordingly, the frames 21, 22 can be rotated in a synchronous fashion with accuracy.

Meanwhile, when the motor 26 is rotated in a state the motor 12 is shut down, the spur gear 25 rotates. In this case, because the frame 22 remains in the current position due to the shutdown of the motor 12, the spur gear 25 moves along the curved surface of the arc gear 22a through the meshing of between the arc gear 22a and the spur gear 25. The moving force of the spur gear 25 is directly conveyed to the reduction gear 27. Consequently, the frame 21 is pushed by means of the reduction gear 27, to rotate the frame 21. Namely, in this state, the frame 21 rotates relatively to the frame 22 being at rest.

In this manner, the first embodiment allows for achieving well the concentricity and enabling a synchronous rotation with accuracy and easiness while enabling both operations of rotating the X-ray tube device 23 and the detector unit 28 in a synchronous fashion and of rotating the X-ray tube device 23 with the detector unit 28 placed at rest.

Second Embodiment

Figure 4:
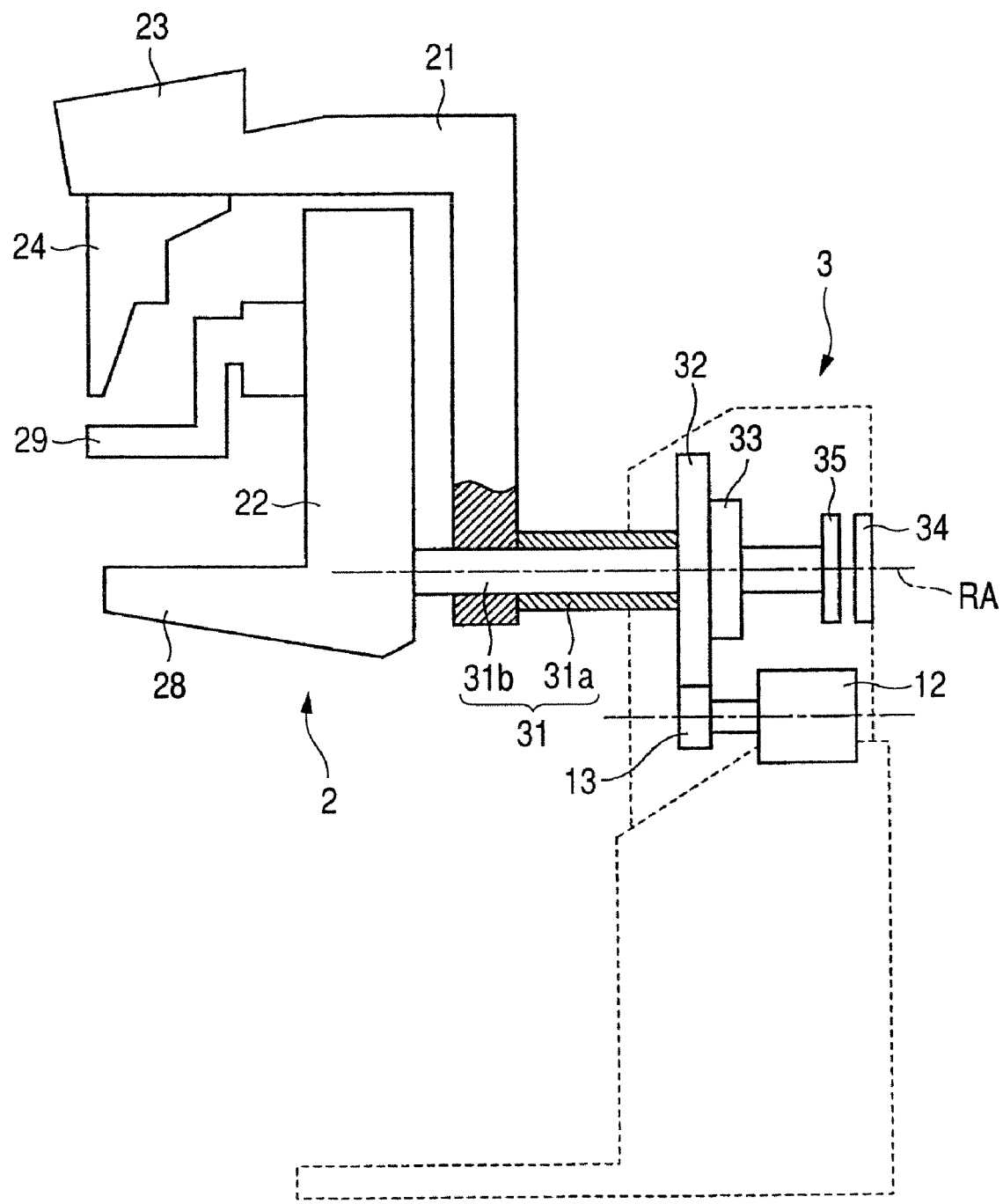
FIG. 4 is a view showing a construction of a mammographic apparatus according to a second embodiment in a first status of operation.

FIG. 4 is a view showing a construction of a mammographic apparatus according to a second embodiment. Note that, in FIG. 4, the corresponding elements to those of FIGS. 1 to 3 are attached with the identical reference numerals, to omit the detailed explanation thereof.

The mammographic apparatus shown in FIG. 4 includes a C-arm unit 2 and a column unit 3. Namely, the mammographic apparatus in the second embodiment is provided with the column unit 3 in place of the column unit 1 of the mammographic apparatus of the first embodiment. Incidentally, FIG. 4 shows a frame 21 partly broken away, together with the internal arrangement of the column unit 1.

The C-arm unit 2 is attached to a shaft 31 projecting from the column unit 3. The shaft 31 includes an outer part 31a and an inner part 31b. The outer and inner parts 31a, 31b are both formed cylindrical thus being coincident at the axes thereof. The outer part 31a is made rotatable regardless of the inner part 31b by the well-known technique, e.g. arranging a bearing between the outer part 31a and the inner part 31b.

The outer part 31a has one end secured to the frame 21. The other end of the outer part 31a is secured to the gear 32. The inner part 31b has one end secured to the frame 22. A tooth clutch 33 is firmly fixed on the inner part 31b at an intermediate portion thereof. The tooth clutch 33 is arranged in a position close to the gear 32.

The gear 32 is in mesh with the gear 13, by means of the teeth formed in the peripheral surface thereof. The gear 32 is formed with teeth, for meshing with the tooth clutch 33, on a surface opposite to the side the outer part 31a is secured. The tooth clutch 33 has a part allowed to move reciprocally in a direction along the rotary axis RA. The movable portion has a tip formed with teeth for meshing with the teeth provided in the gear 32.

The inner part 31b has an end, on the opposite side to the end to which the frame 22 is secured, where a clutch plate 35 is fixed. In the vicinity of the clutch plate 35, an electromagnetic brake 34 is arranged opposite to the clutch plate 35.

In the state shown in FIG. 4, the tooth clutch 33 is locked while the electromagnetic brake 34 is open. In the case the motor 12 is rotated in such a state, the rotation force of the motor 12 is conveyed through the gears 13, 32, to thereby rotate the outer part 31a. As a result, the frame 21 is caused to rotate. Meanwhile, because the tooth clutch 33 is being in mesh with the gear 32, the rotation force of the motor 12 is conveyed through the gears 13, 32 and the tooth clutch 33. Because the electromagnetic brake 34 is not locking the clutch plate 35, the inner part 31b is also rotated with a result that the frame 22 is rotated. Namely, in this state, the frames 21, 22 rotate in a synchronous fashion. In this case, because both the frames 21, 22 rotate about the rotary axis RA, concentricity is achieved well. Meanwhile, because the frames 21, 22 are rotated only by the rotation force of the motor 12, there is no need to control a plurality of motors synchronously. Accordingly, the frames 21, 22 can be rotated in a synchronous fashion with accuracy.

Figure 5:
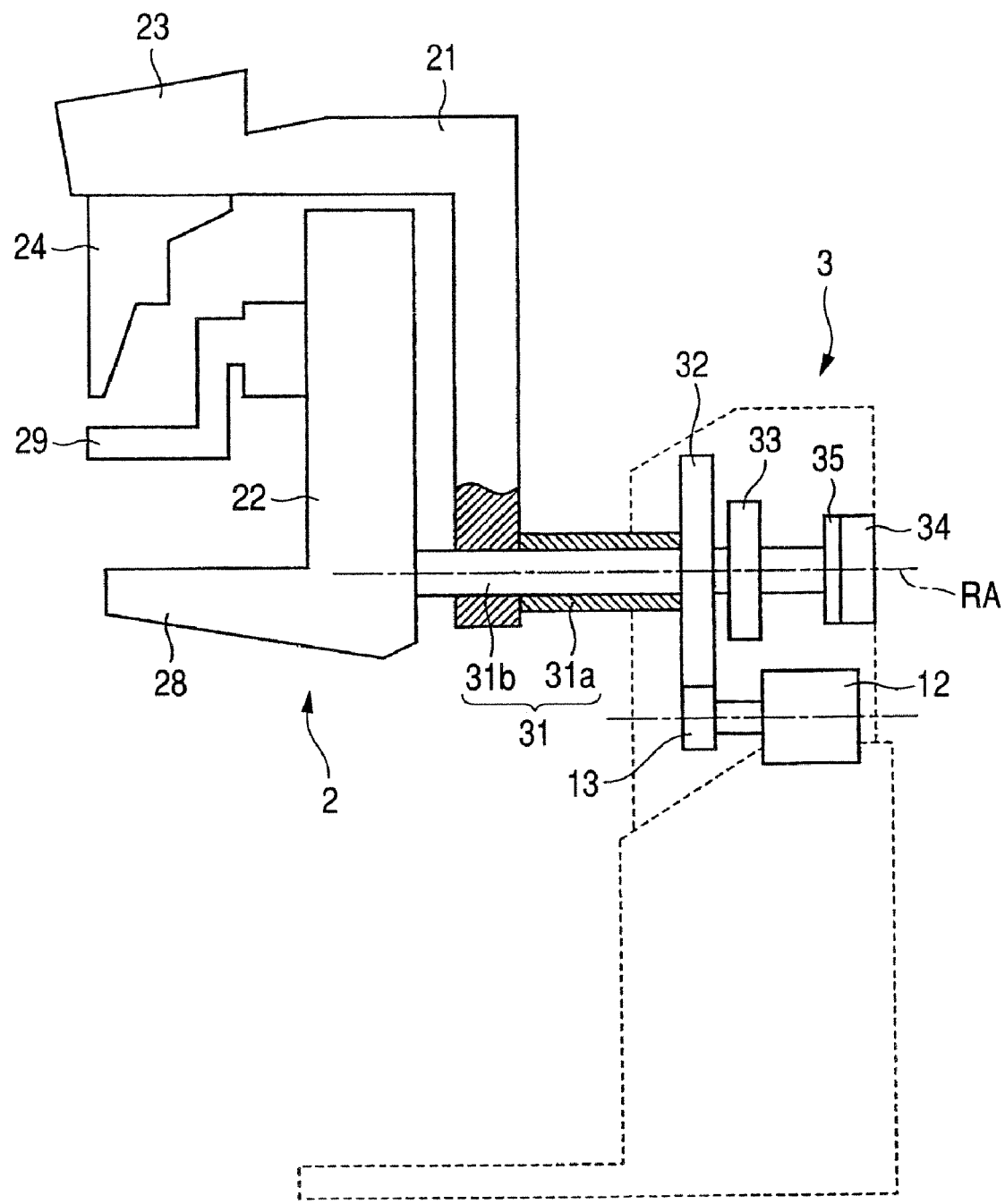
FIG. 5 is a view showing the construction of the mammographic apparatus according to the second embodiment in a second status of operation.

In the state shown in FIG. 5, the tooth clutch 33 is open while the electromagnetic brake 34 is locked. In the case the motor 12 is rotated in this state, the rotation force of the motor 12 is conveyed through the gears 13, 32, to thereby rotate the outer part 31a. As a result, the frame 21 is rotated. However, because the tooth clutch 33 is not being in mesh with the gear 32, the rotation force of the motor 12 is not conveyed to the inner part 31b. Moreover, the electromagnetic brake 34 locks the clutch plate 35. Accordingly, the inner part 31b is not rotated and hence the frame 22 is not rotated. Namely, in this state, the frame 21 rotates relative to the frames 22 being at rest.

Figure 6:
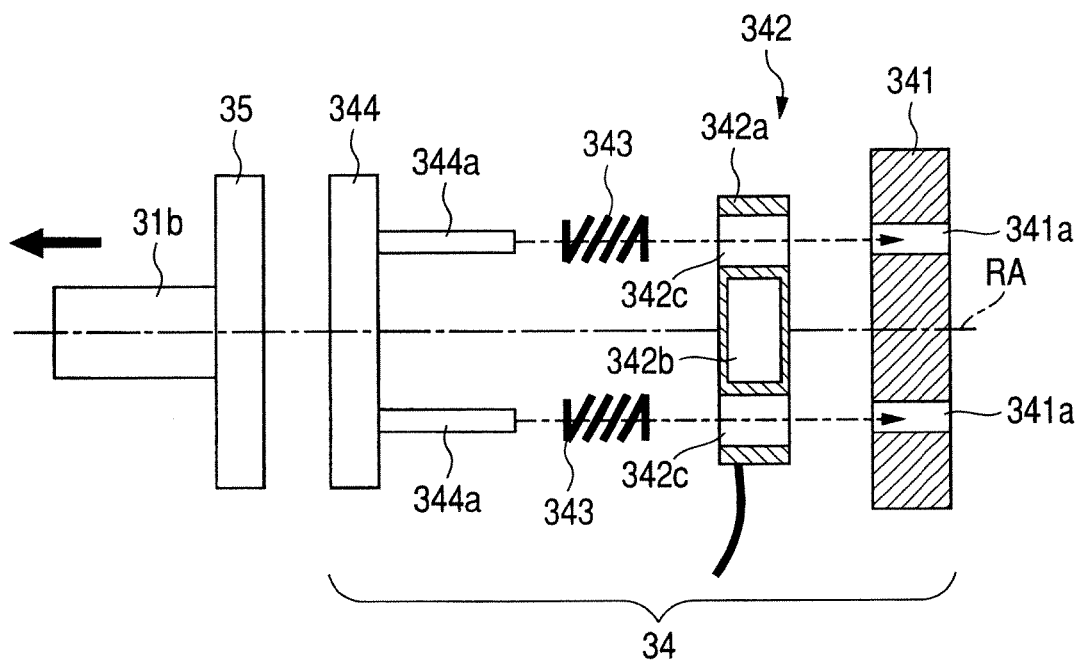
FIG. 6 is an exploded view showing a structure of an electromagnetic brake of FIGS. 4 and 5.

FIG. 6 is an exploded view showing a structure of the electromagnetic brake 34.

The electromagnetic brake 34 includes a base plate 341, an electromagnet unit 342, a plurality of springs 343 and a clutch plate 344, as shown in FIG. 6. In FIG. 6, the base plate 341 and the electromagnet unit 342 are shown by broken away.

The base plate 341 is secured to a housing or the like of the column unit 3. The base plate 341 is formed with a plurality of holes 341a nearly parallel with the rotary axis RA.

The electromagnet unit 342 is structured by receiving an electromagnet 342b in a cylindrical case 342a. The case 342a is formed with a plurality of holes 342c nearly parallel with the rotary axis RA. The electromagnet unit 342 is attached to the base plate 341 in a state the plurality of holes 342c respectively communicate with the plurality of holes 341a.

The plurality of springs 343 are arranged respectively in the plurality of holes 342c.

The clutch plate 344 is formed of metal and arranged oppositely to the clutch plate 35. The clutch plate 344 has a plurality of pins 344a projecting nearly vertically from a surface thereof oppositely to the surface facing to the clutch plate 35. The plurality of pins 344a are inserted in the plurality of holes 341a through the interiors of the plurality of springs 343 arranged in the plurality of holes 342c, respectively.

Figure 7:
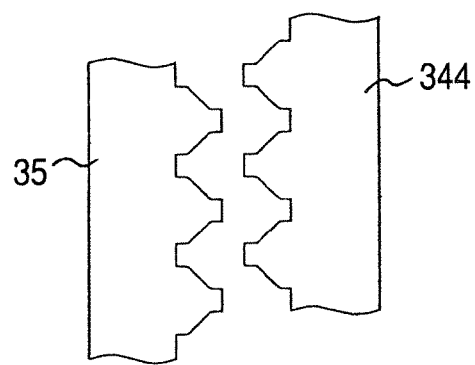
FIG. 7 is a view showing a concavo-convex formed in the FIG. 6 clutch plates.

In each of the clutch plate 344, 35, there is formed a concavo-convex for meshing as shown in FIG. 7. The concavo-convex is provided in a manner to suppress the clutch plate 35 from rotating when placed in meshing with each other.

Figure 8:
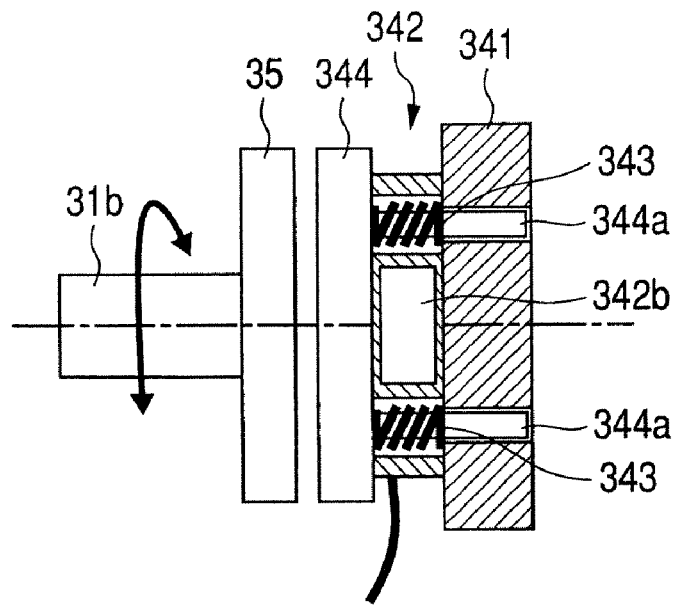
FIG. 8 is a view showing the electromagnetic brake in an open state.

FIG. 8 shows a view illustrating the electromagnetic brake 34 being open.

In the open state, the electromagnet 342b is energized as shown in FIG. 8. Consequently, the clutch plate 344 is magnetically attracted by the electromagnet 342b, thus being detached from the clutch plate 35. In this state, the clutch plate 344 and the clutch plate 35 are not placed in engagement with each other at their concavo-convexes, thus allowing the clutch plate 35 and hence the inner part 31b of the shaft 31 to rotate.

Figure 9:
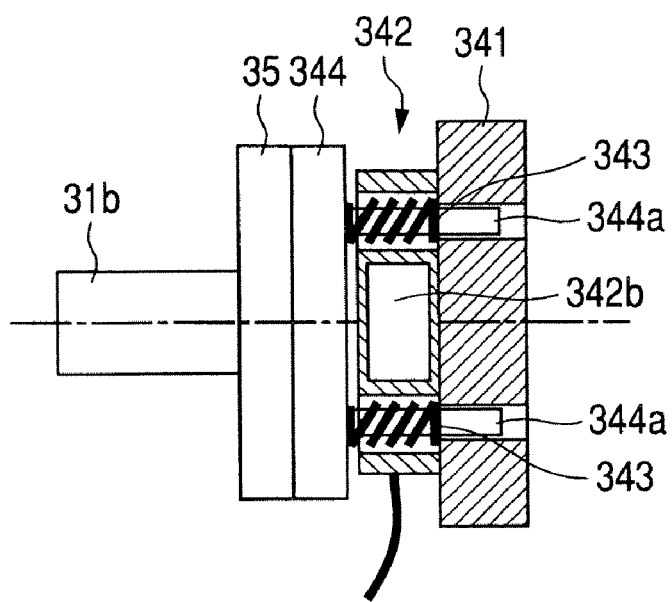
FIG. 9 is a view showing the electromagnetic brake in an locked state.

FIG. 9 shows a view illustrating the electromagnetic brake 34 being locked.

In the locking state, the electromagnet 342b is not energized as shown in FIG. 9. Consequently, the clutch plate 344 is urged on the clutch plate 35 by means of the springs 343. In this state, the clutch plate 344 and the clutch plate 35 are placed in engagement with each other at their concavo-convexes, thus preventing the clutch plate 35 and hence the inner part 31b of the shaft 31 from rotating.

In this manner, the second embodiment allows for achieving well the concentricity and enabling a synchronous rotation with accuracy and easiness while enabling both operations of rotating the X-ray tube device 23 and the detector unit 28 in a synchronous fashion and of rotating the X-ray tube device 23 with the detector unit 28 placed at rest.

Meanwhile, the second embodiment can reduce the number of the components to be arranged to the frame 21 as compared to those of the first embodiment. As a result, the second embodiment can reduce the rotation torque for the frame 21 as compared to that of the first embodiment, thus relieving the motor 12 of load. Meanwhile, the second embodiment can reduce the size of the C-arm unit as compared to that of the first embodiment, thus enabling to lessen the suppression feeling to the subject.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A mammographic for taking an image of a breast of a subject, comprising:
   an X-ray tube for radiating X-rays;
   an X-ray detector for detecting the X-rays radiated from the X-ray tube and transmitted through the breast;
   a column;
   a first support frame arranged, for rotation about a rotary axis, on the column and supporting the X-ray tube;
   a second support frame arranged, for rotation about the rotary axis, on the column and supporting the X-ray detector; and
   a mechanism for selectively switching over between a first mode that the second support frame is rotated by a rotation force of the first support frame and a second mode that the first support frame is rotated independently of the second support frame,
   wherein the mechanism further includes a first motor for rotating the second support frame, a first gear in an arcuate form fixed on the second support frame, a second gear rotatably provided in the first support frame and placed in mesh with the first gear, and a second motor for rotating the second gear.

2. A mammographic apparatus according to claim 1, wherein the mechanism comprises suppressing means that suppresses the second frame from rotating in the second mode.

3. A mammographic apparatus according to claim 2, wherein the suppressing means comprises a self-locking function and is made as a gear unit that delivers a force of the second motor to the second gear.

4. A mammographic apparatus for taking an image of a breast of a subject, comprising:
   an X-ray tube for radiating X-rays;

an X-ray detector for detecting the X-rays radiated from the X-ray tube and transmitted through the breast;

a column;

a first support frame arranged, for rotation about a rotary axis, on the column and supporting the X-ray tube;

a second support frame arranged, for rotation about the rotary axis, on the column and supporting the X-ray detector; and a mechanism for selectively switching over between a first mode that the second support frame is rotated by a rotation force of the first support frame and a second mode that the first support frame is rotated independently of the second support frame, wherein the mechanism further comprises a motor for rotating the second support frame, and a clutch that delivers a rotation force of the motor to the first support frame in the first mode but does not deliver the same rotation force to the first support frame in the second mode.

5. A mammographic apparatus according to claim 4, further comprising suppressing means that suppresses the second support frame from rotating in the second mode.

6. A mammographic apparatus according to claim 5, wherein the suppressing means comprises an electromagnetic brake.

* * * * *